(12) United States Patent
Yang et al.

(10) Patent No.: US 6,902,894 B2
(45) Date of Patent: Jun. 7, 2005

(54) MUTATION DETECTION ON RNA POLMERASE BETA SUBUNIT GENE HAVING RIFAMPIN RESISTANCE

(75) Inventors: Mengsu Yang, Hong Kong (CN); Hok Sin Woo, Hong Kong (CN)

(73) Assignee: Genetel Pharmaceuticals Ltd., Hong Kong (CN)

(*) Notice: Subject to any disclaimer, the term of this patent is extended or adjusted under 35 U.S.C. 154(b) by 208 days.

(21) Appl. No.: 09/949,041

(22) Filed: Sep. 7, 2001

(65) Prior Publication Data

US 2003/0104387 A1 Jun. 5, 2003

(51) Int. Cl.$^7$ .......................... C12Q 1/68; C12P 19/34; C17H 21/02; C17H 21/04
(52) U.S. Cl. ........................ 435/6; 435/91.1; 435/91.2; 435/287.2; 536/23.1; 536/23.7; 536/24.1; 536/24.3
(58) Field of Search ............................... 435/5, 6, 518, 435/287.2

(56) References Cited

U.S. PATENT DOCUMENTS

| | | | |
|---|---|---|---|
| 5,643,723 A | 7/1997 | Persing et al. | |
| 5,789,173 A | 8/1998 | Peck et al. | |
| 5,851,763 A | 12/1998 | Heym et al. | |
| 6,228,575 B1 * | 5/2001 | Gingeras et al. | 435/5 |
| 6,312,960 B1 * | 11/2001 | Balch et al. | 436/518 |
| 6,329,138 B1 * | 12/2001 | De Beenhouwer et al. | 435/6 |
| 6,465,178 B2 * | 10/2002 | Chappa et al. | 435/6 |

OTHER PUBLICATIONS

Erlich et al., "PCR Technology, Principles and Applications for DNA Amplification" May 21, 1991.*
Mikhailovich et al, Journal of Clinical Microb. vol. 39, No. 7, Jul. 2001 pp. 2531–2540.*
Towards Fully Automated Genome-Wide Polymorphism Screening, Nature Genetics, vol. 9, Apr. 1995.
A Primer-Guided Nucleotide Incorporating Assay in the Genotyping of Apolipoprotein E, Syvanen et al., Genomics 8, 684–692 (1990).

(Continued)

Primary Examiner—Jeffrey Fredman
Assistant Examiner—Sally A Sakelaris
(74) Attorney, Agent, or Firm—Wallenstein Wagner & Rockey, Ltd.

(57) ABSTRACT

The present invention provides a diagnostic test method for detecting a tendency to rifampin resistance caused by mutations in a rpoB gene of *M. tuberculosis*, comprising the steps of (i) extracting genomic DNA from a biological sample containing *M. tuberculosis* cells; (ii) amplifying from the extracted genomic DNA the rpoB gene coding sequence or at least one distinct fragment thereof containing nucleotides encoding at least one test amino acid of the group consisting of amino acid numbers 511, 512, 513, 514, 515, 516, 517, 518, 522, 526, 529, 531, 533 to produce fluorescently labeled amplification product; (iii) contacting said fluorescently labeled amplification product with a first control array of oligonucleotide probes having DNA sequences specific to the wildtype *M. tuberculosis* rpoB gene coding sequence, including the nucleotides encoding the at least one test amino acid, and with a second test array of oligonucleotide probes having DNA sequences specific to the *M. tuberculosis* rpoB gene coding sequence, including nucleotides encoding mutations in the at least one test amino acid, wherein at least 3 mutations of the rpoB gene are probed for by the second test array of oligonucleotide probes; detecting any fluorescent hybridization signal of said purified fluorescently labeled amplification product which hybridized with the first and second arrays of oligonucleotide probes; (iv) correlating said detected hybridization with a tendency to rifampin resistance; and (v) correlating the detected hybridization to a tendency to rifampcin resistance and MDR.

19 Claims, 9 Drawing Sheets

(3 of 9 Drawing Sheet(s) Filed in Color)

OTHER PUBLICATIONS

Minisequencing: A Specific Tool for DNA Analysis and Diagnostics on Oligonucleotide Arrays, Pastinen et al.; Genome Research, 7:606–614 (1997).

Fluorescence Energy Transfer Detection as a Homogeneous DNA Diagnostic Method, Chen et al; *Proc. Natl. Acad. Sci. USA*, vol. 94, pp. 10756–10761, Sep. 1997.

Fluorescence Polarization in Homogeneous Nucleic Acid Analysis, Chen et al., Genome Research, 9:492–498 (1999).

Single–Well Genotyping of Diallellic Sequence Variations by a Two–Color ELISA–based Oligonucleotide Ligation Assay, Tobe et al., 3728–32, *Nucleic Acids Research*, 1996, vol. 24, No. 19.

Multicolor Molecular Beacons for Allele Discrimination, Tyagi et al., *Nature Biotechnology*, vol. 16, Jan. 1998.

Large–Scale Identification, Mapping and Genotyping of Single–Nucleotide Polymorphisms in the Human Genome, Wang et al., *Science*, vol. 280, May 15, 1998.

Dynamic Allele–Specific Hybridization, Howell et al., *1999 Nature Biotechnology, Inc.*, vol. 17, Jan. 17, 1999.

Evaluation of Single Nucleotide Polymorphism Typing with Invader on PCR Amplicons and its Automation, Mein et al., Genome Research, 10:330–343 (2000).

PCR—A Practical Approach, Quirke et al., Feb. 1991.

*DNA Cloning*, vol. 1, A Practical Approach.

DNA Sequencing with Chain–Terminating Inhibitors, Sanger et al., *Proc. Natl. Acad. Sci. USA*, vol. 74, No. 12, pp 5463–67, Dec. 1977.

Using Antibodies—A Laboratory Manual, Harlow.

*General Techniques of Cell Culture*, Harrison et al., published 1997.

*Phage Display of Peptides and Proteins*—A Laboratory Manual, published 1996.

Isolation of Genomic DNA from Mycobacteria, Belisle et al., from *Methods in Molecular Biology*, vol. 101, Mycobacteria Protocols.

Molecular Evidence for Heterogenity of the Multiple–Drug–Resistant Mycobacterium Tuberculosis Population in Scotland (1990 to 1997), Zang et al., *Journal of Clinical Microbiology*, Apr. 1999, pp 998–1003, vol. 37, No. 4.

Simultaneous Genotyping and Species Identification Using Hydridization Pattern Recognition Analysis of Generic Mycobacterium DNC Arrays, Gingeras et al., Genome Research 1998, 8:435–448 (1998).

Bioconjugate Techniques, Hermanson.

Mutations in the rpoB Gene of Rifampin–Resistant Mycobacterium Tuberculosis Strains Isolated Mostly In Asian Countries and Their Rapid Detection by Line Probe Assay, Hirano et al., *Journal of Clinical Microbiology*, Aug. 1999, p 2663–66, vol. 37, No. 8.

SBE–Tags: An Array–Based Method for Efficient Single–Nucleotide Polymorphism Genotyping, Hirschhorn et al., *PNAS*, Oct. 24, 2000, vol. 97, No. 22.

Detection of a Genetic Locus Encoding Resistance to Rifamph in Mycobacterial Cultures and in Clinical Specimens, Hunt et al., Diagn Microbiol Infect Dis 1994, 18:219–27.

Characterization by Automated DNC Sequencing of Mutations in the Gene (rpoB) Encoding the RNA Polymerase B Subunit in Rifampin–Resistant Mycobacterium Tuberculosis Strains for New York City and Texas, *Journal of Clinical Microbiology*, Kapur et al., Apr. 1994, p 1095–98, vol. 32, No. 4.

The rpoB Gene of Mycobacterium Tuberculosis, Miller et al., *Antimicrobial Agents and Chemotherapy*, Apr. 1994; p 805–11, vol. 38, No. 4.

Detection of Resistance to Isoniazid, Rifampin and Streptomycin in Clinical Isolates of Mycobacterium Tuberculosis by Molecular Methods, Nachamkin et al., Clinical Infectious Diseases, 1997, 24:894–00.

rpoB Mutations in Multidrug–Resistant Strains of Mycobacterium Tuberculosis Isolated in Italy, *Journal of Clinical Microbiology*, Apr. 1999, p 1197–99, vol. 37, No. 4.

Evaluation of the INNO–LIPA Rif. TB Assay, a Reserve Hydridization Assay for the Simultaneous Detection of Mycobacterium Tuberculosis Complex and Its Resistance to Rifampin, Rossau et al., *Antimicrobial Agents and Chemotherapy*, Oct. 1997, p 2093–98, vol. 41, No. 10.

Mycobacterium Species Identification and Rifampin Resistance Testing with High–Density DNA Probe Arrays, Troesch et al., *Journal of Clinical Microbiology*, Jan. 1999, p 49–55, vol. 37, No. 1.

Direct, Automated Detection of Rifampin–Resistant Mycobacterium Tuberculosis by Polymerase Chain Reaction and Single–Strand Conformation Polymorphism Analysis, Talenti et al., *Antimicrobial Agents and Chemotherapy* Oct. 1993, p 2054–58, vol. 37, No. 10.

Characterization of Rifampin Resistance in Pathogenic Mycobacteria, Williams et al., *Antimicrobial Agents and Chemotherapy*, Oct. 1994, p 2380–86, vol. 38, No. 10.

Evaluation of a Polymerase Chain Reaction–Based Universal Heteroduplex Generator Assay for Direct Detection of Rifampin Susceptibility of Mycobacterium Tuberculosis from Sputum Specimens, Williams et al., Clinical Infectious Diseases, 1998, 26:446–50.

\* cited by examiner

FIG. 3

| MTB | Blank | M2 | M2 | M3 | M3 | MTB |
|---|---|---|---|---|---|---|
| M4 | M4 | M5 | M5 | M7 | M7 | MTB |
| M8 | M8 | M9 | M9 | M10 | M10 | MTB |
| M11 | M11 | M12 | M12 | M13 | M13 | MTB |
| M14 | M14 | M15 | M15 | M16 | M16 | MTB |
| M17 | M17 | M18 | M18 | M20 | M20 | MTB |
| M22 | M22 | M26 | M26 | M27 | M27 | MTB |
| M28 | M28 | M29 | M29 | M30 | M30 | MTB |
| M31A | M31A | M31B | M31B | M31C | M31C | MTB |
| M32D | M32D | M34 | M34 | M35E | M35E | MTB |
| M37 | M37 | M38 | M38 | W1 | W1 | MTB |
| W2 | W2 | W3 | W3 | W4 | W4 | MTB |
| W5A | W5A | W6 | W6 | W7 | W7 | MTB |
| W8C | W8C | W9 | W9 | W10 | W10 | MTB |
| Blank | Blank | W11 | W11 | W12 | W12 | MTB |

Rif$^R$ TB, H526D

C (TAMRA) → G (Cy5)

Rif$^R$ strain    Rif$^S$ strain 0.82    −1.27

$$\text{Genotype\_score} = \log_{10} \frac{(\text{fraction mutant allele dye} + 0.01)}{(\text{fraction wildtype allele dye} + 0.01)}$$

MUTATION DETECTION ON RNA POLMERASE BETA SUBUNIT GENE HAVING RIFAMPIN RESISTANCE

FIELD OF THE INVENTION

The present invention is directed to a method of detecting mutation of RNA polymerase beta subunit gene having rifampin resistance and a kit for performing such method.

BACKGROUND OF INVENTION

Tuberculosis (TB), caused by the bacterium, *Mycobacterium tuberculosis*, has re-emerged as a major infectious disease worldwide and an estimated 2 million people died from the disease annually. For example, in Hong Kong alone, it has in recent years accounted for the greatest number of cases of all noticeable infectious diseases, totaling about 7,000 cases a year. The first-line anti-tuberculosis drug regimen, consisting of rifampin, isoniazid, pyrazinamide, ethambutol and streptomycin, is generally effective if adhered to as prescribed. However, the antibiotic treatment usually lasts for 6 to 8 months and the unpleasant side-effects can lead to non-compliance to the prescribed regimen, which may in turn result in the selection of resistant organisms and therefore treatment failure. This partly contributes to the emergence of multidrug-resistant strains of *M. tuberculosis* (MDR-MTB). Since early 1990s, outbreaks of MDR-MTB have been reported with increasing frequency, especially among human immuno-deficiency virus-positive patients in the United States and Europe. It has been shown that MDR-MTB are genetically diverse, which suggest that they may be unrelated to each other and had probably evolved independently (Z. Fang et al., J. Clin. Microbiol. 1999; 37:998–1003, PMID 10074516). Recent surveys in Hong Kong indicated multidrug resistance in 0.2 to 0.6% of MTB isolates.

As outbreaks of MDR-MTB often lead to high mortality, the need for rapid identification of drug resistance has increased. Furthermore, when a diagnosis of TB is confirmed, early initiation of chemotherapy is desirable in order to prevent complications in the patient and transmission of TB to others. Drug susceptibility testing is required by clinicians to choose the most effective anti-tuberculosis agents and to evaluate patient's response to chemotherapy. However, many current susceptibility tests, which usually involve culturing the slow-growing mycobacteria in the presence of antibiotics, take a rather long period of 5 to 14 days. Various other tests have been available, some of them are rather complicated and involve sequencing a portion of the gene of a sample. Kapur, V. et al. (J. Clin. Mocrobiol. 1999; April; 32(4):1095–8, PMID No. 8027320) have used automated DNA sequencing to characterize mutations associated with rifampin resistance in a 69-bp region of the gene, rpoB, encoding the beta subunit RNA polymerase in *M. tuberculosis*. U.S. Pat. No. 5,643,723 discloses a detection of a genetic locus encoding resistance to rifampin in Mycobacterial cultures. This detection method also comprises a sequencing step to determine the presence or absence of *M. tuberculosis* or mutants. U.S. Pat. No. 5,789,173 discloses a method for anti-microbial susceptibility testing to screen antibiotics. This method does provide a more rapid anti-microbial susceptibility testing to screen different antibiotics. U.S. Pat. No. 5,851,763 discloses a detection method of antibiotic resistance in *M. tuberculosis*. In this prior art, DNA sequences from *M. tuberculosis* are analyzed by Southern blotting and hybridization. In particular, DNA fragments can be separated on agarose gels and denatured in situ. The fragments can then be transferred from the gel to a water insoluable solid, porous support or an activated cellulose paper.

DNA mutations in the genes conferring resistance to anti-tuberculosis drugs have been identified, and include thirty-two base substitutions, four deletions and two insertion mutations have been detected in a central segment of the rpoB gene. This is shown in FIGS. 1 and 2. These mutations are believed to confer resistance to rifampin by decreasing the binding affinity of rifampin to the β-subunit of RNA polymerase. Rifampin inhibits transcription upon binding to the bacterial RNA polymerase. A method disclosed by Telenti A., et al. (Antimicrob Agents Chemother 1993 October; 37(10):2054–8, PMID No. 8257122) were able to detect all seventeen different rifampin known mutations at that time.

The present invention provides a method which can rapidly detect at least some known mutations in the RNA polymerase beta subunit (rpoB) gene. For instance, the method according to the present invention allows detection of the mutations in as short as 1 to 2 days which is significantly shorter than 5 to 14 days for using antibiotics susceptibility test with which culturing slow growing bacteria is needed. Further, the method is easy to perform and is therefore desirably cost effective to be performed on a large-scale basis. The results produced therefrom are also reliable and readily detectable. This is due to the use of both control and test arrays to compete for the same amplification products. In an unlikely event that the control and test arrays produce contradictory results, it can easily be detected and minimal mis-diagnosis results. Finally, it is envisaged that the present invention is easily adapted to automation.

SUMMARY OF THE INVENTION

As resistance to rifampin in *M. tuberculosis* appears to be correlated with MDR-MTB, rifampin resistance may be used as a marker for MDR-MTB (K. Hirano et al, J Clin. Microbiol. 37:2663–2666(1999)). In fact, various rifampin resistance of MDR-MTB of rpoB gene is detactable by the method described in the present invention.

According to a first aspect of the present invention, there is provided a diagnostic test method for detecting a tendency to rifampin resistance caused by mutations in a rpoB gene of *M. tuberculosis*, comprising the steps of (i) extracting genomic DNA from a biological sample containing *M. tuberculosis* cells; (ii) amplifying from the extracted genomic DNA the rpoB gene coding sequence or at least one distinct fragment thereof containing nucleotides encoding at least one test amino acid of the group consisting of amino acid numbers 511, 512, 513, 514, 515, 516, 517, 518, 522, 526, 529, 531, 533 to produce fluorescently labeled amplification product; (iii) contacting the fluorescently labeled amplification product with a first control array of oligonucleotide probes having DNA sequences specific to the wildtype *M. tuberculosis* rpoB gene coding sequence, including the nucleotides encoding the at least one test amino acid, and with a second test array of oligonucleotide probes having DNA sequences specific to the *M. tuberculosis* rpoB gene coding sequence, including nucleotides encoding mutations in the at least one test amino acid, wherein at least 3 mutations of the rpoB gene are probed for by the second test array of oligonucleotide probes; (iv) detecting any fluorescent hybridization signal of the purified fluorescently labeled amplification product which hybridized with the first and second arrays of oligonucleotide probes; (v) correlating the detected hybridization with a tendency to rifampin resistance; and (vi) correlating the detected hybridization to a tendency to rifampcin resistance and MDR.

Preferably, the amplification may comprise a step of performing polymerase chain reaction (PCR) using ingredients including at least one of the extracted genomic DNA, DNA polymerase, uracil N-glycosylase, and deoxy- and/or dideoxy-nucleotides and primer pair designed from the DNA sequence of the rpoB gene. In step (ii), the amplification product may be subject to purification.

More particularly, the amplification may comprise a further step of linear amplification producing the fluorescently labeled amplification product.

Advantageously, in step (ii), a single based extensions procedure may be performed to amplify products of said PCR.

Suitably, the oligonucleotides may be immobolized on a substrate. The substrate may be a glass slide. The substrate may contain amine reactive groups.

The oligonucleotide probes may be modified with C6 amine at their 5' end.

More particularly, the surface of the substrate may contain carboxyl groups activated by substantially 0.4–1.0 M 1-Ethyl-3-(3-dimethylaminopropyl)carbodiimide hydrochloride and 0.1–1.0 M N-Hydroxysuccinimide on which the oligonucleotide probes immobilize.

The amplification in step (ii) may amplify the coding sequence plus 5' promoter region of said rpoB gene.

The PCR may be subject to substantially an initial condition of 50° C. for 20 seconds, and then 95° C. for 9 minutes and 40 seconds, subsequently followed by 45 cycles of denaturation at 95° C. for 20 seconds, 63° C. for 20 seconds, 72° C. for 20 seconds, and a final step of 15 minutes.

More particularly, the substrate, prior to hybridization, may be treated with ethanoamine. The oligonucleotide probes may be treated with 1-Ethyl-3-(3-dimethylaminopropyl)carbodiimide hydrochloride (EDC) and/or N-hydroxysuccinimide (NHS) prior to immobolization on the substrate.

In the PCR, a pair of primers used may be selected from a group having DNA sequences of SEQ ID NOs. 2 and 3.

In the step of linear amplification, a primer used may have the DNA sequence of SEQ ID NO. 1, and amplification product resulting therefrom may be fluorescently labeled.

In the single base extensions procedure, a pair of primers used may be selected from a group having DNA sequences of SEQ ID NOs. 48 and 49, SEQ ID NOs. 50 and 51, and SEQ ID NOs. 52 and 53, and the amplification product resulted therefrom may fluorescently labeled.

The amplification product may be fluorescently labeled with a fluorophore.

The fluorescently labeled amplification product can be contacted with the first and second arrays of oligonucleotide probes under conditions in which a quantifiably greater amount of it hybridizes any of the oligonucleotide probes which are complementary to it than hybridizes the oligonucleotide probes which are non- complementary to it. For example, at least 2, 3, 4, 5, 6, 7, 8, 9, 10, 15, 20, 25 or 50 times as much of the fluorescently labeled amplification product may hybridize the oligonucleotide probes which are complementary to it than hybridizes the oligonucleotide probes which are non-complementary to it. An example of such conditions is stringent hybridization conditions.

The first control array of oligonucleotide probes may have DNA sequences selected from the group consisting SEQ ID NOs. 4–15. The second test array of oligonucleotide probes may have DNA sequences selected from the group consisting SEQ ID NOs. 16–46.

The fluorescent hybridization signal may be detectable by a scanning device.

According to a second aspect of the present invention, there is provided a diagnostic test kit for performing the diagnostic test method described above.

The kit may comprise various ingredients for performing the amplification. More particularly, the kit may comprise reagents for performing the PCR including at least one of the group consisting DNA polymerase, uracil N-glycosylase, deoxy- and/or dideoxy-nucleotides, and a pair of primers.

Preferably, the kit may comprise a substrate on which the oligonucletides are immobilized. The substrate may be a glass slide. More particularly, the substrate may contain amine reactive groups. The oligonucleotide probes may have amino C6 modification at their 5' end.

The kit may comprise a pair of primers used in a first amplification step having the DNA sequences of SEQ ID NOs. 2 and 3. The kit may comprise a primer used in a second amplification step having the DNA sequence of SEQ ID NO. 1.

The kit may comprise a pair of primers for used in an single base extension amplification procedure selected from a group having DNA sequences of SEQ ID NOs. 48 and 49, SEQ ID NOs. 50 and 51, and SEQ ID NOs. 52 and 53.

The kit may comprise a first control array immobilized with oligonucleotide probes having DNA sequences selected from the group consisting of SEQ ID NOs. 4–15. The kit may comprise a second test array immobilized with oligonucleotide probes having DNA sequences selected from the group consisting SEQ ID NOs. 16–46. The oligonucleotide probes may have amino C6 modification at their 5' end.

The kit may comprise a pair of primers for used in a first set of amplification selected from a group consisting of the DNA sequences of SEQ ID NOs. 2 and 3. The kit may comprise a primer used in a second set of amplification having the DNA sequence of SEQ ID NO. 1.

A kit may comprise a pair of primers for use in a single base extension amplification procedure selected from a group consisting of the DNA sequences of SEQ ID NOs. 48 and 49, SEQ ID NOs. 50 and 51, and SEQ ID NOs. 52 and 53.

BRIEF DESCRIPTION OF THE DRAWINGS

The patent or application file contains at least one drawing executed in color. Copies of this patent or patent application publication with drawing(s) will be provided by the Office upon request and payment of the necessary fee.

The invention will be further apparent from the following description with reference to the figures, which shows by way of examples the detection method according to the present invention.

FIG. 3 is a grid showing a location of each of the oligonucleotide probes (see e.g. Table 1).

DETAILED DESCRIPTION OF THE INVENTION

Figure 1:
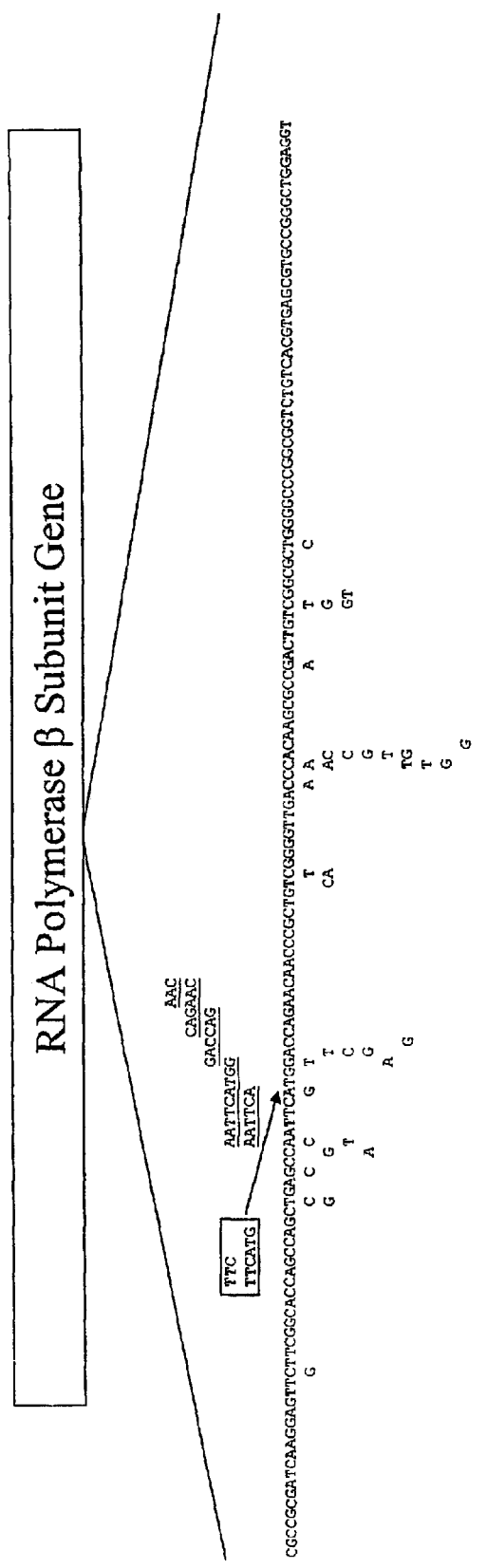
FIG. 1 is a partial nucleotide sequence of the rpoB from *M. tuberculosis* corresponding to the central portion amplified with primer pair RPO3 (SEQ ID NO. 2) and RPO4 (SEQ ID substitutions, deletions (underlined) and insertions (boxed). The DNA sequence leading up to the primer RPO4 (SEQ ID NO. 3) binding site has not been shown due to space constraint. The sequence as shown equates to nucleotides 2236–2479 of PubMed sequence accession no. L27989.
Figure 2:
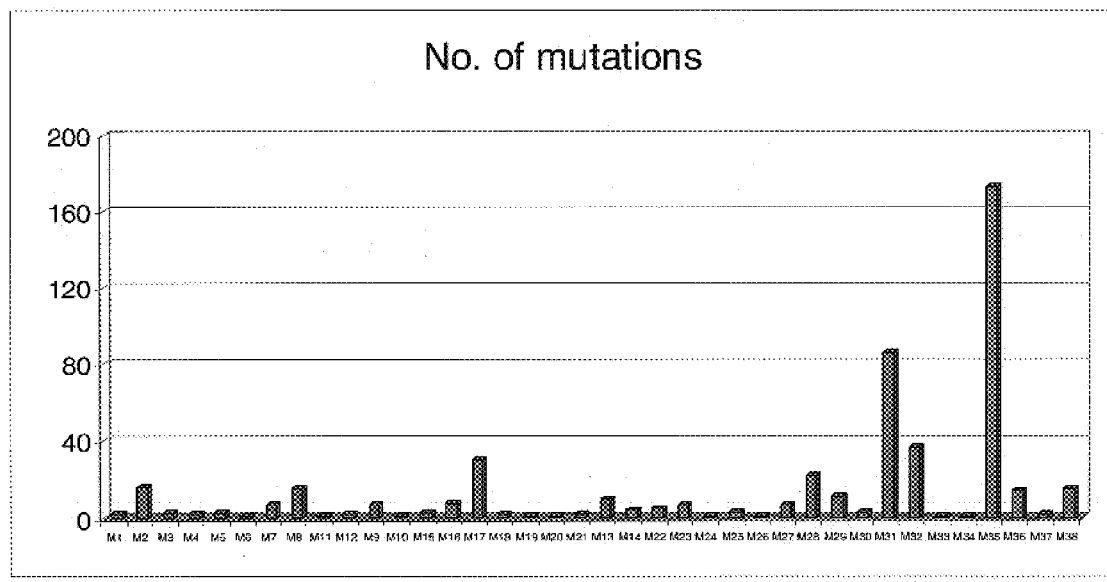
FIG. 2 is a chart summarizing the results of a global survey of occurrence of various mutations that are targeted by a microarray on which the present invention is based.

The present invention is directed to a method of detecting mutation of RNA polymerase beta subunit gene having rifampin resistance and a kit for conducting such method. This gene was originally isolated by Miller L P et al. (Antimicrob Agents Chemother, 1994 April; 38(4):805–11, PMID 8031050). A number of mutations in this gene are known. FIG. 1 is a diagram showing a partial nucleotide sequence of the rpoB gene from *M. tuberculosis*. The DNA sequence corresponds to the central portion amplified with primers RPO3 (SEQ ID NO. 2) and RPO4 (SEQ ID NO. 3). FIG. 1 also shows the nature and positions of some of the known mutations, including base substitutions, deletions (underlined) and insertions (boxed). It has previously been shown that one short region of the rpoB gene has an unusually high frequency of insertions and deletions (Kapur, V. et al., J. Clin. Mocrobiol., 1994 Apr; 32(4): 1095–8, PMID No. 8027320). As can be seen, the sequence of the primer RPO3 matches the first 18 bases of the gene shown in FIG. 1. The primer RPO4 binds to a site 205–224 bases down stream from the 5' end of primer RPO3. The DNA sequence leading up to the primer RPO4 (SEQ ID NO. 3) binding site has not been shown in FIG. 1 due to space constraint.

The method according to the present invention generally involves a step of amplification of genomic DNA (or a distinct fragment thereof) obtained from a biological sample containing *M. tuberculosis* cells. A number of amplification approaches such as polymerase chain reaction (PCR) together with linear amplification may be used. Alternatively, a single base extensions (SBE) approach may also be used. As far as PCR is concerned, the following guidelines can be used in determining PCR reaction conditions and reagents. Firstly, a plurality of oligonucleotide probes is used. The oligonucleotide probes are designed according to the following guidelines:

one probe for each known mutation

For each probe, the sequence should be the same as the sense strand, and the mutation positioned around the center of the probe.

For each polymorphic position, one positive control probe specific for the wildtype sequence, with polymorphic sites positioned around the center of the probe.

The probes should be preferably 15 bases in length.

The oligonucleotide should have an amino C6 modification at its 5' end, be purified by HPLC, a final yield of about 40 nmol.

Table 1 provides a detailed description of these probes.

Based on these guidelines, two arrays (a control array and a test array) of oligonucleotide probes have been designed. As indicated above, the probes are preferably 15 bases in length. However, the actual length of any particular probe may vary according to the empirical hybridization behavior. For example, 13 mers, 14 mers and 16 mers can also be used. For example, probe M35E (SEQ ID NO. 44) is a 13 mer; probes M31A, M31B & M32D are 14 mers (SEQ ID NOs. 39, 40 & 42 respectively); and probe W5A (SEQ ID NO. 8) is a 16 mer. The first array is the control array which includes the wildtype oligonucleotide probes of W1, W2, W3, W4, W5A, W6, W7, W8, W9, W10, W11 and W12, its sequences are shown in the sequence listing (SEQ ID NOs. 4–15 respectively). The second array is the test array which includes the mutant oligonucleotide probes of M2, M3, M4, M5, M7, M8, M9, M10, M11, M12, M13, M14, M15, M16, M17, M18, M20, M22, M26, M27, M28, M29, M30, M31A, M31B, M31C, M32D, M34, M35E, M37 and M38, its sequences are shown in the sequence listing (SEQ ID NOs. 16–46 respectively). M32D, M34, M35E, M37 and M38, its sequences are shown in the sequence listing (SEQ ID NOs. 16–46 respectively).

The method also involves the use of the two primers for PCR RPO3 (SEQ ID NO. 2) and RPO4 (SEQ ID NO. 3). The PCR primers have been designed with the assistance of the Primer 3 program provided online by National Center for Biotechnology Information, Bethesda, Md., the specificity of which was checked against the GenBank nucleotide sequence database by the Blast program. The first primer, namely RPO3 is an 18-mer which is identical to the first 18 bases of the sequence shown in FIG. 1. The second primer, namely RPO4, binds to a site 205–224 bases downstream from the 5' end of primer RPO3.

The method further involves the use of microscope slides containing amine reactive groups. The microscope slides are treated with succinic anhydride for the introduction of carboxylate groups to enable subsequent amine coupling chemistry. Succinic anhydride is reacted with the surface amine groups in a ring-opening process, creating an amide bond and forming a terminal carboxylate. Succinic anhydride (0.5 g) is first dissolved in 2 ml of dioxane by gentle heating, and then mixed with 100 ml of 0.5 M phosphate buffer, pH 7.6. The slides are then immersed in the succinic anhydride mixture overnight at RT. The slides are then rinsed 5 times in distilled water, and then dried by centrifugation at 1,000 rpm for 3 min.

The method is now explained by way of the following examples.

EXAMPLE 1

Differential Hybridization Approach

Extraction of Genomic DNA

For use in preliminary experiments, genomic DNA was extracted from the MTB standard strain H37 by the method of Belisle and Sonnenberg (Methods Mol Biol. 1998; 101:31–44, PMID: 9921467). DNA of clinical isolates was extracted by commercially available DNA extraction kit, such as the Qiagen's QIAamp blood kit. DNA concentrations were estimated by comparing amounts of fluorescence of the DNA preparations with that of a DNA mass standard in ethidium bromide-stained agarose gel. The DNA extract was stored at 4° C.

PCR Amplification

PCR was performed in a PTC 100 thermal cycler (MJ Research). A 50-μl reaction contained 1 μM each of primers, 10 ng of genomic DNA, 0.2 mM of each of dUTP, dATP, dCTP and dGTP, 1.5 mM $MgCl_2$, 10 mM Tris-HCl (pH 8.3), 50 mM KCl, 1 units of uracil N-glycosylase and 5 units of AmpliTaq Gold DNA polymerase. After the reaction was set up in a thin-walled tube, thermal cycling was carried out as follows: 50° C. for 2 min, 95° C. for 9 min 40s, followed by 45 cycles of denaturation at 95° C. for 20s, annealing at 63° C. for 20s and extension at 72° C. for 20s, and a last extension step of 15 min. It is to be noted that while the entire rpoB gene may be amplified, a distinct fragment thereof is actually sufficient. The distinct fragment should be sufficient cover the potential regions with mutations and in any event, the distinct fragment is of at least 10 nucleotides in length and preferably of at least more than 13 nucleotides which is the length of one of the shortest oligonucleotide probe (M35E, SEQ ID NO. 44) shown in the sequence listing.

Linear Amplification

After the PCR product was cleaned up using a PCR Product Purification Spin Column (for example, QIAGEN's QIAquick Spin Column), the purified PCR product was used as template in linear amplification with only one primer of which RPO2 (SEQ ID NO. 41) is used. The PE Applied Biosystems dRhodamine cycle sequencing kit may be used. Fluorescently labeled DNA was provided which was used subsequently in hybridization. Alternatively, the PCR product resulted from the initial PCR step could be used as template in linear amplification with only the RPO2 primer that had been labeled with Cy3 at its 5' end. The fluorescent label results from Cy3 which is a fluorophore. It is to be noted that the amplification product is substantially of a single strandedness.

The amplified DNA potentially contains nucleotides encoding at least one test amino acid of the group consisting of amino acid numbers 511, 512, 513, 514, 515, 516, 517, 518, 522, 526, 529, 531, 533.

Preparation of Microarray

Prior to immobilization on glass slide surface, the oligonucleotide probes (200 μM) that had been modified with C6 amino group at 5' end were mixed with an equal volume of 0.4–1.0 M EDC (1-Ethyl-3-(3-dimethylaminopropyl) carbodiimide hydrochloride) and 0.1–1.0 M NHS (N-Hydroxysuccinimide). The 5' amino group, in the presence of EDC and NHS, reacted with the carboxylate group that was introduced onto the slide surface by succinic anhydride, to form a stable amide bond. The C6 short chain served as a spacer to enhance steric accommodation of the immobilized oligonucleotide probe. The probe array (shown in FIG. 3) containing duplicate spots of each probe was prepared using an X-Y-Z positioning robotic system. The printed slides were incubated at 37° C. inside a humidity chamber overnight, washed with 0.2% SDS for 5 min and rinsed with distilled water five times.

Prior to hybridization, the slide was treated with 1 M ethanolamine, pH 8.5, for 8 min at RT so as to block the remaining carboxyl groups. After denaturation in a boiling water bath for 2 min, 11 μl of hybridization solution containing non-purified linear amplification product, 5×SSC and 0.2% SDS was applied on the microarray, then a plastic coverslip was lowered onto the microarray, and the slide was sealed with HybriWell Chamber.

Hybridization

The hybridization was carried out under the following conditions. The hybridization was carried out overnight at 42° C. Unbound DNA and heteroduplex containing mismatch were removed by washing in 1×SSC and 0.1% SDS at room temperature for 10 min and 0.5×SSC for 10 min. The slide was dried by centrifugation at 1000 rpm for 3 min. Hybridization signal was detected using a scanning device such as the ScanArray 4000.

The same procedures were performed for three other mutant strains, namely, Mutant Strain C (D516V), Mutant Strain D (S531L) and Mutant Strain E (H526D). Genomic DNA for each of these strains is extracted using the same procedures.

Results

Figure 4:
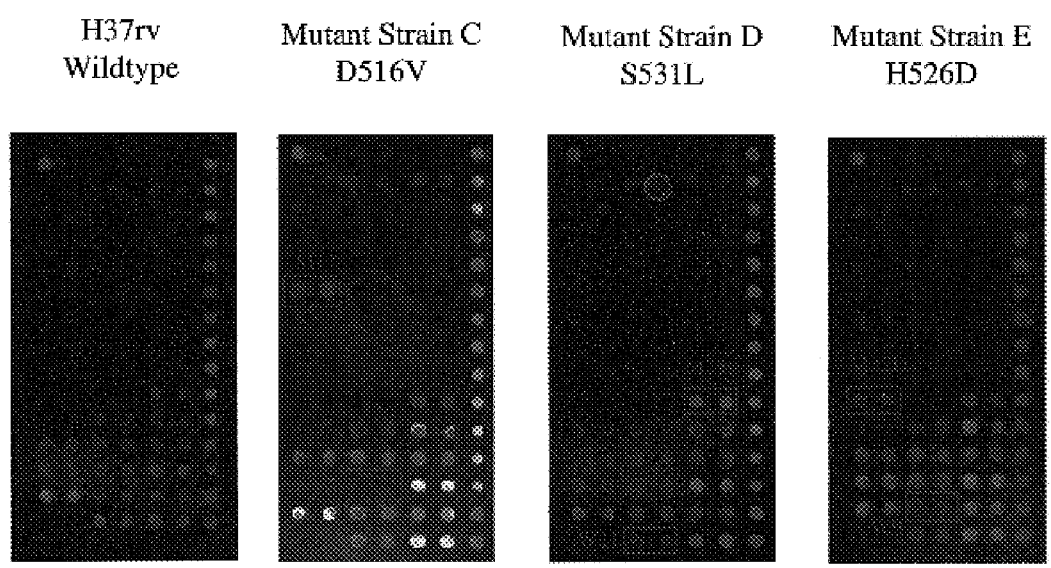
FIG. 4 shows various images of hybridization patterns obtained with microarrays. The spots at the top left corner of each array and at the first column on the night side contained an oligonucleotide probe (SEQ ID NO. 47) specific for a conserved sequence within the amplicon that was used as a location marker. The probes specific for the mutant sequence and the wildtype sequence are on the upper part and the lower part of the microarray respectively (refer to FIG. 3 for the detailed probe identity).

In FIG. 4, the image on the left of the page labeled with "Wild Type (H37rv)" shows an array of the detection of the hybridization signals. This is used as a comparison to other arrays of hybridization signals generated from other mutant types *M. tuberculosis*. All four images together shown in FIG. 4 indicate the arrays of the hybridization signals resulting from the experiments with the wild type and three mutant strains. The location of each probe is indicated on FIG. 3. It can be seen that each array adopts a 105 well (7×15) format.

For the rifampin-sensitive MTB strain H37rv, the probes specific for the mutant sequence showed a weak but detectable (i.e. quantifiable) signal.

For the rifampin-resistant MTB strain C carrying a D516V mutation, there was an increase of signal from mutant probe M17 and a decrease of signal from wildtype probe W6.

For rifampin-resistant MTB strain D carrying a S531L mutation, there was an increase of signal from mutant probe M35E and a decrease of signal from wildtype probe W11.

For the rifampin-resistant MTB strain E carrying a H526D mutation, there was an increase of signal from mutant probe M32D and a decrease of signal from wildtype probe W9.

Figure 5:
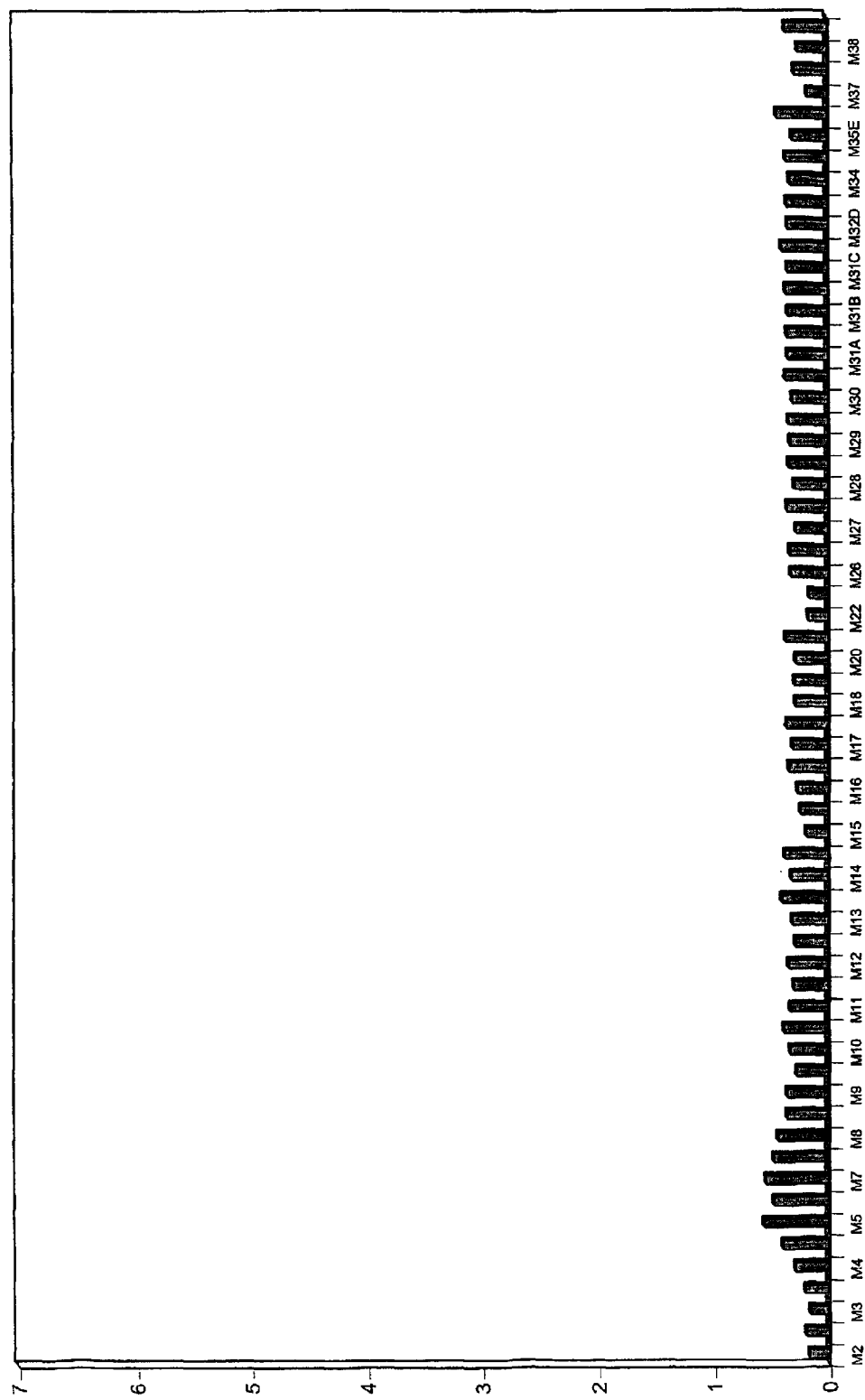
FIG. 5 shows the result of a rifampin-sensitive MTB strain H37rv carrying no mutation. The y values correspond to the mutant-to-wildtype ratio, which was calculated as the fluorescence reading of the mutant probe divided by the fluorescence reading of the corresponding wildtype probe.
Figure 6:
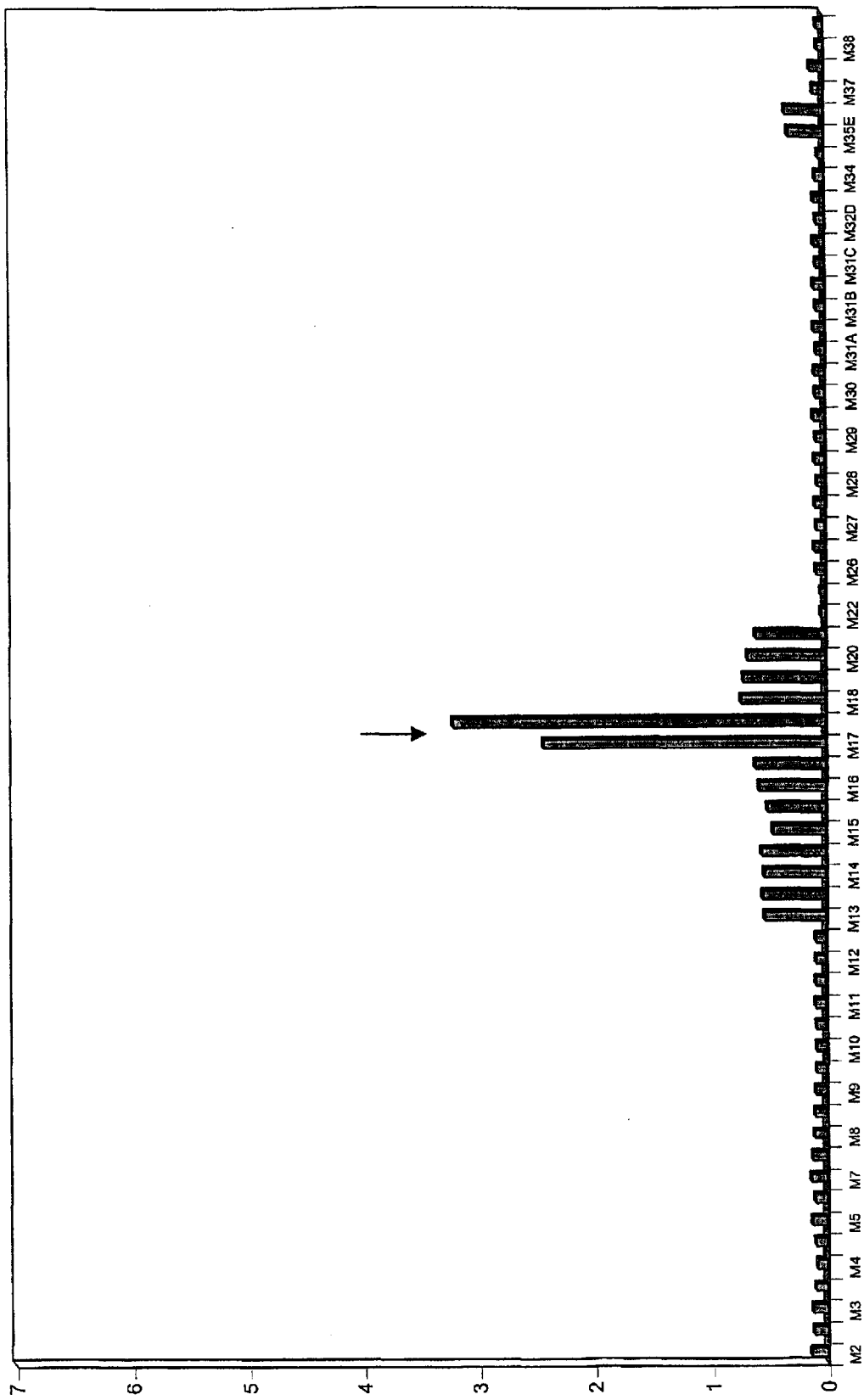
FIG. 6 shows the result of a rifampin-resistant MTB strain carrying a D516V mutation. The y values correspond to the mutant-to-wildtype ratio, which was calculated as the fluorescence reading of the mutant probe divided by the fluorescence reading of the corresponding wildtype probe.
Figure 7:
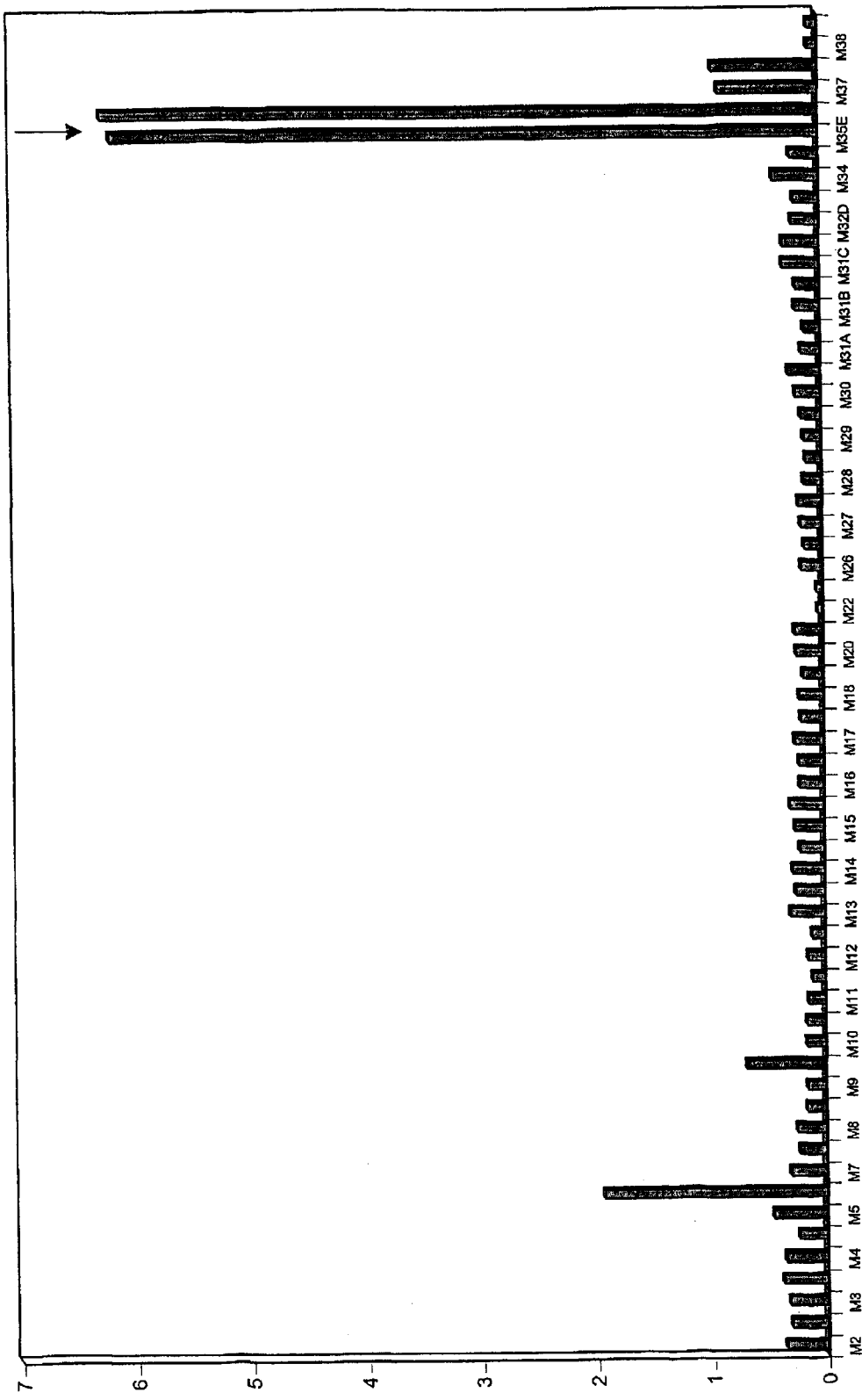
FIG. 7 shows the result of a rifampin-resistant MTB strain carrying a S531L mutation. The y values correspond to the mutant-to-wildtype ratio, which was calculated as the fluorescence reading of the mutant probe divided by the fluorescence reading of the corresponding wildtype probe.
Figure 8:
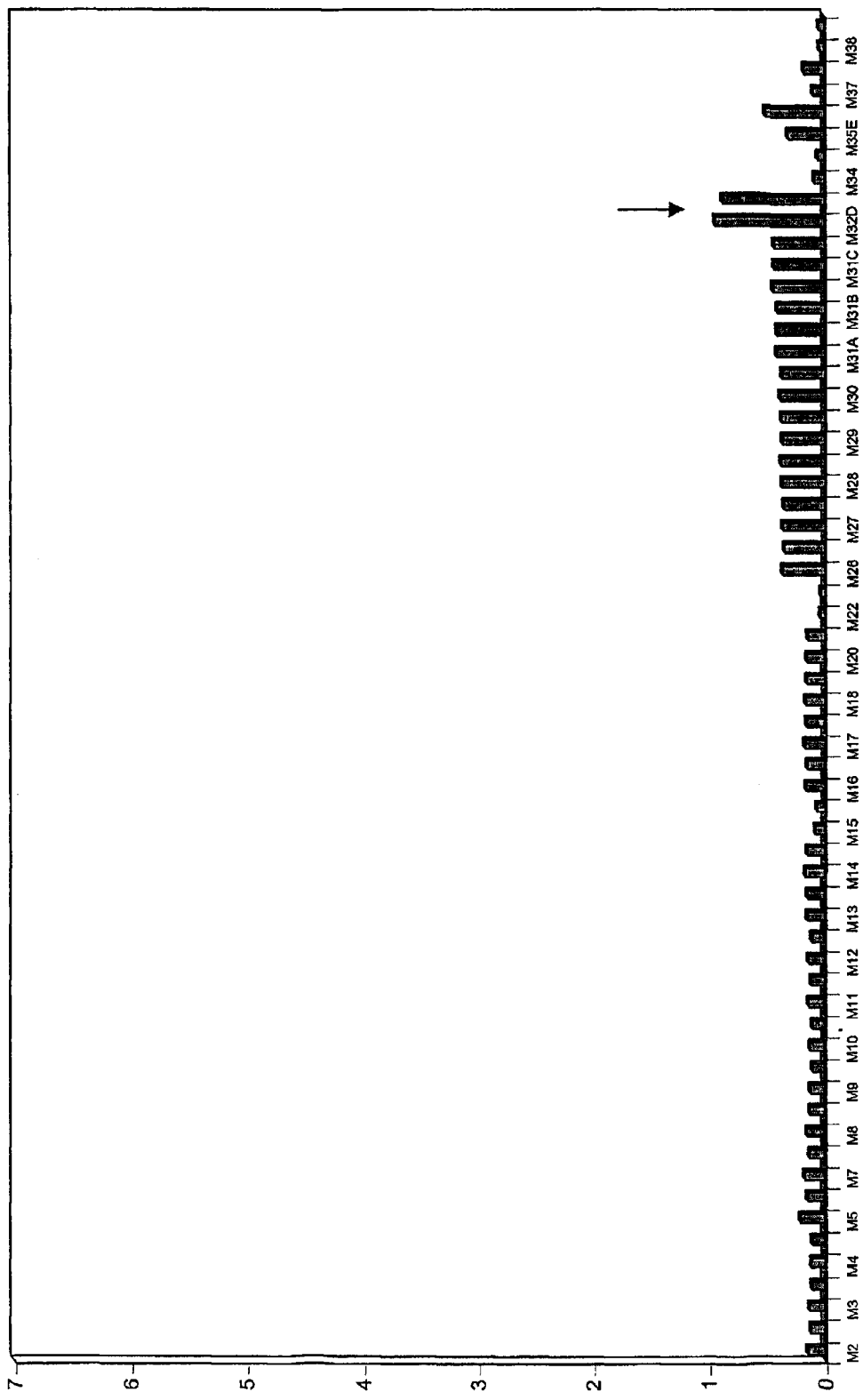
FIG. 8 shows the result of a rifampin-resistant MTB strain carrying a H526D mutation. The y values correspond to the mutant-to-wildtype ratio, which was calculated as the florescence reading of the mutant probe divided by the fluorescence reading of the corresponding wildtype probe.

These results are expressed quantitatively in the bar charts of FIGS. 5 to 7.

EXAMPLE 2

Single Base Extension Approach

As an alternative to the differential hybridization approach used above, the single base extension may also be used.

SNPs (single nucleotide polymorphisms) can be genotyped using a wide range of technologies, including single base extension (SBE, also called minisequencing or template-directed incorporation) (Syvanen A C et al., Genomics. 1990 December; 8(4):684–92, PMID: 2276739; Pastinen T et al., Genome Res. 1997 June; 7(6):606–14, PMID: 9199933; Chen X et al., PNAS USA. Sep. 30, 1997;94(20):10756–61, PMID: 9380706; Chen X et al., Genome Res. 1999 May; 9(5):492–8, PMID: 10330129), 5' exonuclease assays such as TaqMan (Livak K J et al., Nat Genet. 1995 April; 9(4):341–2, PMID: 7795635), oligonucleotide ligation (Tobe V O et al., Nucleic Acids Res. Oct. 1, 1996;24(19):3728–32, PMID: 8871551), molecular beacons (Tyagi S et al., Nat Biotechnol. 1998 Jan; 16(1):49–53, PMID: 9447593), differential hybridization (Wang DG et al., Science. May 15, 1998;280(5366):1077–82, PMID: 9582121; Howell W M et al., Nat Biotechnol. 1999 January; 17(1):87–8, PMID: 9920276), and cleavage by a flap endonuclease (Invader (Mein C A et al., Genome Res. 2000 March; 10(3):330–43, PMID: 10720574)). Particularly useful for the large-scale genotyping of SNPs is SBE-TAGS (Hirschhorn J N et al., PNAS USA Oct. 24, 2000; 97(22):12164–9, PMID: 11035790).

The single base extension is potentially more robust than the differential hybridization approach, because the specificity of the primer extension is determined by the DNA polymerase, in contrast to that of differential hybridization, which is based on the relatively unpredictable effect of a single base mismatch on the melting temperature of the hybridized DNA.

Extension primers used in this approach of this invention were designed according to the following guidelines:

A theoretical melting temperature of about 55° C.

The 3' end is positioned immediately adjacent to the mutation.

The coding strand is used where possible.

3 sets of SBE primers and corresponding capture probes were designed specifically to detect the 3 particular mutations that have been identified in Hong Kong patients. These extension primers were H526D & H526D-CP (SEQ ID Nos. 48 & 49 respectively), S531L &S531L-CP (SEQ ID NOs. 50 & 51 respectively), D516V & 516V-CP (SEQ ID NOs. 52 & 53 respectively).

Single Base Extensions

After obtaining the PCR product using the same procedures as in the differential hybridization approach, 10 µl of PCR product mixture was added to 5 µl of SBE mix containing 0.1 M Tris (pH 9.5), 4 mM MgCl$_2$, 1 pmol of each SBE primer, 2 U of thermosequenase, and 5 pmol each of TAMRA-ddATP, TAMRA-ddCTP, Cy5-ddGTP and ROX-ddUTP. The SBE reaction included 30 cycles of denaturation (96° C. for 30 s), annealing (50° C. for 30 s) and extension (60° C. for 1 min).

Five µl of the SBE reaction was mixed with 1 µl of mix containing 8×SSC, salmon sperm DNA (0.2 mg/ml) and 0.4% SDS, and then added to the microarray of capture probes. The capture probes were simply the reverse complement of the SBE primers plus an addition of 15 dT to the 5' end. After a coverslip trimmed to the size of the microarray was lowered, the slide was placed inside a humidity chamber to prevent drying and was incubated at 50° C. for 4 h. The slide was washed in 2×SSC, 0.1% SDS for 5 min at room temperature, followed by 3 brief rinses in 2×SSC and a final wash in 0.2×SSC for 1 min. After the array was spun dry at 1300 rpm for 5 min, it was scanned using the ScanArray 4000.

Results and Explanation

Figure 9:
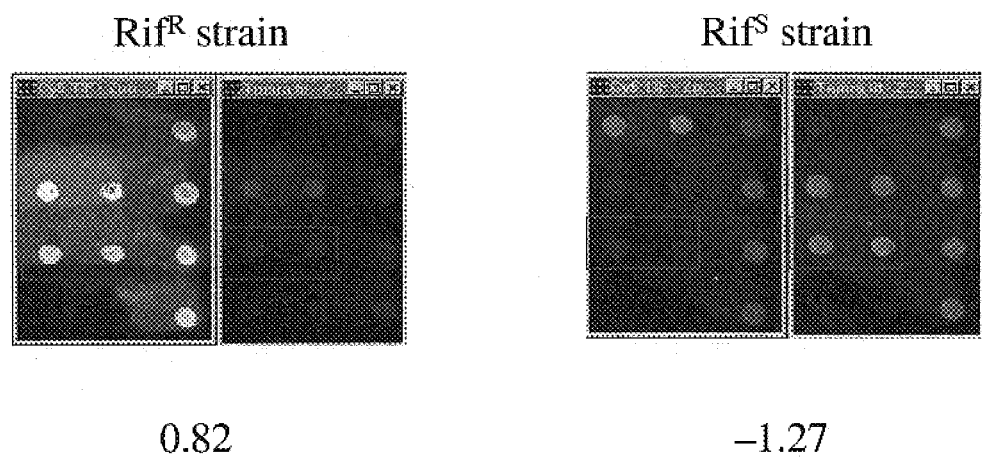
FIG. 9 shows the result of a rifampin-resistant MTB strain carrying a H526D mutation obtained by an alternate approach.

Experiments were done using the above three pairs of extension primer detecting the presence of mutation. FIG. 9 shows single base extension results of a rifampin-resistant MTB strain carrying a H526D mutation. In the single base extension reaction, the dideoxy C was labeled with the TAMRA dye, whereas the dideoxy G was labeled with the Cy5 dye. When there was mutation causing resistance, the primer was extended with a G carrying Cy5 dye, therefore, the spot containing the capture probe gave strong signal in Cy5 channel, but weak signal from the TAMRA. For the rifampin sensitive strain where the mutation was absent, the TAMRA signal was stronger than the Cy5 signal. The result was expressed in terms of the genotype score, calculated as the ratio of the two dyes. Since the log function was used, a genotype score of 1 or −1 represented an actual ratio of 10.

The genotype score was calculated as follows:

$$\log_{10} \frac{\text{(fraction mutant allele dye} + 0.01)}{\text{(fraction wildtype allele dye} + 0.01)}$$

Cutoff was set at +0.5 and −0.5, a score above +0.5 and one below −0.5 indicates the presence and absence of the mutation respectively.

Other SNP genotyping methods which produce fluorescently labeled polynucleotide amplification products can be used in the methods of the invention and include 5' exonuclease assays such as TaqMan, oligonucleotide ligation, molecular beacons and cleavage by flap endonuclease.

The above DNA microarray-based detection does not require culture of the slow-growing mycobacteria as in the conventional susceptibility testing. Lastly, DNA microarray technology is amenable to automation.

Unless stated otherwise, all procedures were performed using standard protocols and following manufacturer's instructions where applicable. Standard protocols for various techniques including PCR, molecular cloning, manipulation and sequencing, the manufacture of antibodies, epitope mapping and mimotope design, cell culturing and phage display, are described in texts such as McPherson, M. J. et al. (1991, PCR: A practical approach, Oxford University Press, Oxford), Sambrook, J. et al. (1989, Molecular cloning: a laboratory manual, Cold Spring Harbour Laboratory, New York), Huynh and Davies (1985, "DNA Cloning Vol I—A Practical Approach", IRL Press, Oxford, Ed. D. M. Glover), Sanger, F. et al. (1977, PNAS USA 74(12): 5463–5467), Harlow, E. and Lane, D. ("Using Antibodies: A Laboratory Manual", Cold Spring Habour Laboratory Press, New York, 1998), Jung, G. and Beck-Sickinger, A. G. (1992, Angew. Chem. Int. Ed. Eng., 31:367–486), Harris, M. A. and Rae, I. F. ("General Techniques of Cell Culture", 1997, Cambridge University Press, ISBN 0521 573645), "Phage Display of Peptides and Proteins: A Laboratory Manual" (Eds. Kay, B. K., Winter, J., and McCafferty, J., Academic Press Inc., 1996, ISBN 0-12-402380-0).

Reagents and equipment useful in, amongst others, the methods detailed herein are available from the likes of Amersham, Boehringer Mannheim, Clontech, Genosys, Millipore, Novagen, Perkin Elmer, Pharmacia, Promega, Qiagen, Sigma and Stratagene.

Unless otherwise stated, the following teachings may be used in carrying out the experiments of the present invention:

J. T. Belisle et al., "Isolation of Genomic DNA from Mycobacteria," in Mycobacteria Protocols, T. Parish et al., Eds., Humana Press, New Jersey.

Z. Fang et al., "Molecular Evidence for Heterogeneity of the Multiple-Drug-Resistant *Mycobacterium tuberculosis* Population in Scotland (1990 to 1997)," J. Clin. Microbiol. 37:998–1003 (1999).

T. Gingeras et al., "Simultaneous genotyping and species identification using hybridization pattern recognition analysis of generic Mycobacterium DNA arrays," Genome Res. 8:435–48 (1998).

G. T. Hermanson, "Bioconjugate Techniques," Academic Press, California (1996).

K. Hirano et al., "Mutations in the rpoB Gene of Rifampin-Resistant Mycobacterium tuberculosis Strains Isolated Mostly in Asian Countries and Their Rapid Detection by Line Probe Assay," J. Clin. Microbiol. 37:2663–2666 (1999).

J. N. Hirschhorn et al., "SBE-TAGS: An Array-based Method for Efficient Single-nucleotide Polymorphism Genotyping," Proc. Natl. Acad. Sci. 97:12164–12169 (2000).

J. M. Hunt et al., "Detection of a Genetic Locus Encoding Resistance to Rifampin in Mycobacterial Cultures and in Clinical Specimens," Diagn. Microbiol. Infect. Dis. 18:219–227 (1994).

V. Kapur et al., "Characterization by Automated DNA Sequencing of Mutations in the Gene (rpoB) Encoding the RNA Polymerase β Subunit in Rifampin-Resistant *Mycobacterium tuberculosis* Strains from New York City and Texas," J. Clin. Microbiol. 32:1095–1098 (1994).

L. P. Miller et al., "The rpoB Gene of *Mycobacterium tuberculosis*," Antimicrob. Agents Chemother. 38:805–811 (1994).

I. Nachamkin et al., "Detection of Resistance to Isoniazid, Rifampin and Streptomycin in isolates of *Mycobacterium tuberculosis* by Molecular Methods," Clin. Infect. Dis. 24:894–900 (1997).

G. Pozzi et al., "rpoB Mutations in Multidrug-Resistant Strains of *Mycobacterium tuberculosis* Isolated in Italy," J. Clin. Microbiol. 37:1197–1199 (1999).

R. Rossau et al., "Evaluation of the INNO-PiPA Rif. TB Assay, a Reverse Hybridization Assay for the Simultaneous Detection of *Mycobacterium tuberculosis* Complex and Its Resistance to Rifampin," Antimicrob. Agents Chemother. 41:2093–2098 (1997).

A. Troesch et al., "Mycobacterium species identification and rifampin resistance testing with high-density DNA probe arrays." J Clin. Microbiol. 37:49–55 (1999).

A. Telenti et al., "Direct, Automated Detection of Rifampin-Resistant Mycobacterium tuberculosis by Polymerase Chain Reaction and Single-Strand Conformation Polymorphism Analysis," Antimicrob. Agents Chemother. 37:2054–2058 (1993).

D. L. Williams et al., "Characterization of Rifampin Resistance in Pathogenic Mycobacteria," Antimicrob. Agents Chemother. 38:2380–2386 (1994).

D. L. Williams et al., "Evaluation of a Polymerase Chain Reaction-Based Universal Heteroduplex Generator Assay for Direct Detection of Rifampin Susceptibility of *Mycobacterium tuberculosis* from Sputum Specimens," Clin. Infect. Dis. 26:446–450 (1998).

The contents of each of the references discussed herein, including the references cited therein, are herein incorporated by reference in their entirety.

TABLE 1

Comparison of Mutant and Wild Type Probes

| Mutant probe | | Wild type probe | | Amino acid affected (No.)[a] | Amino acid change | Base change |
|---|---|---|---|---|---|---|
| M2 | (SEQ ID NO. 16) | W2 | (SEQ ID NO. 5) | 436 | Leu → Pro | CTG → CCG |
| M3 | (SEQ ID NO. 17) | W2 | (SEQ ID NO. 5) | 436 | Leu → Arg | CTG → CGG |
| M4 | (SED ID NO. 18) | W3 | (SEQ ID NO. 6) | 437 | Ser → Thr | AGC → ACC |
| M5 | (SEQ ID NO. 19) | W4 | (SEQ ID NO. 7) | 438 | Gln → Glu | CAA → GAA |
| M7 | (SEQ ID NO. 20) | W4 | (SEQ ID NO. 7) | 438 | Gln → Pro | CAA → CCA |
| M8 | (SEQ ID NO. 21) | W4 | (SEQ ID NO. 7) | 438 | Gln → Leu | CAA → CTA |
| M11 | (SEQ ID NO. 22) | W4 | (SEQ ID NO. 7) | 438 439 440 | Gln Phe Met deletion, Leu insertion | AAT TCA deletion |
| M12 | (SEQ ID NO. 23) | W4 | (SEQ ID NO. 7) | 439 439 440 441 | Gln Phe Met Asp deletion, His insertion | AAT TCA TGG deletion |
| M9 | (SEQ ID NO. 24) | W4 | (SEQ ID NO. 7) | 439 | Phe insertion | TTC insertion |
| M10 | (SEQ ID NO. 25) | W4 | (SEQ ID NO. 7) | 439 440 | Phe Met insertion | TTC ATG insertion |
| M15 | (SEQ ID NO. 26) | W5A | (SEQ ID NO. 8) | 440 | Met → Val | ATG → GTG |
| M16 | (SEQ ID NO. 27) | W6 | (SEQ ID NO. 9) | 441 | Asp → Tyr | GAC → TAC |
| M17 | (SEQ ID NO. 28) | W6 | (SEQ ID NO. 9) | 441 | Asp → Val | GAC → GTC |
| M18 | (SEQ ID NO. 29) | W6 | (SEQ ID NO. 9) | 441 | Asp → Ala | GAC → GCC |
| M20 | (SEQ ID NO. 30) | W6 | (SEQ ID NO. 9) | 441 | Asp → Glu | GAC → GAA |
| M13 | (SEQ ID NO. 31) | W6 | (SEQ ID NO. 9) | 441 442 | Asp Gln deletion | GAC CAG deletion |
| M14 | (SEQ ID NO. 32) | W6 | (SEQ ID NO. 9) | 443 | Asn deletion | AAC deletion |
| M22 | (SEQ ID NO. 33) | W7 | (SEQ ID NO. 10) | 447 | Ser → Gln | TCG → TTG |
| M26 | (SEQ ID NO. 24) | W9 | (SEQ ID NO. 12) | 451 | His → Thr | CAC → ACC |
| M27 | (SEQ ID NO. 35) | W10 | (SEQ ID NO. 12) | 451 | His → Pro | CAC → CCC |
| M28 | (SEQ ID NO. 36) | W9 | (SEQ ID NO. 12) | 451 | His → Arg | CAC → CGC |
| M29 | (SEQ ID NO. 37) | W9 | (SEQ ID NO. 12) | 451 | His → Leu | CAC → CTC |
| M30 | (SEQ ID NO. 39) | W9 | (SEQ ID NO. 12) | 451 | His → Cys | CAC → TGC |
| M31B | (SEQ ID NO. 40) | W9 | (SEQ ID NO. 12) | 451 | His → Tyr | CAC → TAC |
| M32D | (SEQ ID NO. 42) | W9 | (SEQ ID NO. 12) | 451 | His → Asp | CAC → GAC |
| M34 | (SEQ ID NO. 43) | W10 | (SEQ ID NO. 13) | 454 | Arg → Gln | CGA → CAA |
| M35E | (SEQ ID NO. 44) | W11 | (SEQ ID NO. 14) | 456 | Ser → Leu | TCG → TTG |
| M37 | (SEQ ID NO. 45) | W11 | (SEQ ID NO. 14) | 456 | Ser → Cys | TCG → TGT |
| M38 | (SED ID NO. 46) | W12 | (SEQ ID NO. 15) | 458 | Leu → Pro | CTG → CCG |

[a]Numbering based on *M. tuberculosis* beta-subunit of RNA polymerase (Miller, Crawford and Shinnick 1994, GenBank Accession No. L27989)

What is claimed is:

1. A diagnostic test method for detecting a tendency to rifampin resistance caused by mutations in a rpoB gene of M. tuberculosis, comprising the steps of:
   a) extracting genomic DNA from a biological sample containing M. tuberculosis cells;
   b) amplifying from said extracted genomic DNA the rpoB gene coding sequence or at least one distinct fragment thereof containing nucleotides encoding at least one test amino acid of the group consisting of amino acid numbers 511, 512, 513, 514, 515, 516, 517, 518, 522, 526, 529, 531, 533, said amplification comprising a step of performing polymerase chain reaction (PCR) to produce a fluorescently labeled amplification product;
   c) performing a single based extension procedure to amplify products of said PCR, wherein the pair of primers of SEQ ID Nos. 48 and 49 are used in said single base extension procedure;
   d) contacting said fluorescently labeled amplification product with a first control array of oligonucleotide probes having DNA sequences specific to the wildtype M. tuberculosis rpoB gene coding sequence, including said nucleotides encoding said at least one test amino acid, and with a second test array of oligonucleotide probes having DNA sequences specific to the M. tuberculosis rpoB gene coding sequence, including nucleotides encoding mutations in said at least one test amino acid, wherein at least 3 mutations of the rpoB gene are probed for by said second test array of oligonucleotide probes;
   e) detecting any fluorescent hybridization signal of said purified fluorescently labeled amplification product which hybridized with said first and second arrays of oligonucleotide probes;
   f) correlating said detected hybridization with a tendency to rifampin resistance; and
   g) correlating said detected hybridization to a tendency to rifampcin resistance and MDR.

2. A method as claimed in claim 1 wherein in step (b) said polymerase chain reaction (PCR) uses ingredients including at least one of said extracted genomic DNA, DNA polymerase, uracil N-glycosylase, and deoxy- and/or dideoxy-nucleotides and primer pair designed from the DNA sequence of rpoB gene.

3. A method as claimed in claim 2 wherein after step (b) said amplification product is subject to purification.

4. A method as claimed in claim 2 wherein in step (b) said amplification comprises a further step of linear amplification producing said fluorescently labeled amplification product.

5. A method as claimed in claim 1 wherein said oligonucleotides are immobilized on a substrate.

6. A method as claimed in claim 5 wherein said substrate is a glass slide.

7. A method as claimed in claim 5 wherein said substrate contains amine reactive groups.

8. A method as claimed in claim 1 wherein said oligonucleotide probes are modified with C6 amine at 5' end.

9. A method as claimed in claim 5 wherein surface of said substrate includes carboxyl groups activated by substantially 1-Ethyl-3-(3-dimethylaminopropyl)carbodiimide hydrochloride and N-Hydroxysuccinimide on which said oligonucleotide probes immobilize.

10. A method as claimed in claim 1 wherein said amplification in step (b) amplifies said coding sequence plus 5' promoter region of said rpoB gene.

11. A method as claimed in claim 2 wherein said reaction is subject to substantially an initial condition of 50° C. for 20 seconds, and then 95° C. for 9 minutes and 40 seconds, subsequently followed by 45 cycles of denaturation at 950° C. for 20 seconds, 63° C. for 20 seconds, 72° C. for 20 seconds, and a final step of 15 minutes.

12. A method as claimed in claim 5 wherein said substrate, prior to hybridization, is treated with ethanolamine.

13. A method as claimed in claim 1 wherein said oligonucleotide probes are treated with 1-Ethyl-3-(3-dimethylaminopropyl)carbodiimide hydrochloride (EDC) and/or N-hydroxysuccinimide (NHS) prior to immobilization on said substrate.

14. A method as claimed in claim 2 wherein a pair of primers is used in said PCR, said primers selected from a group having DNA sequences of SEQ ID NOs. 2 and 3.

15. A method as claimed in claim 4 wherein a primer is used in said linear amplification selected from a group having DNA sequence of SEQ ID NO. 1, and amplification product resulted therefrom is fluorescently labeled.

16. A method as claimed in claim 1 wherein said amplification product is fluorescently labeled with a fluorophore.

17. A method as claimed in claim 1 wherein said first control array of oligonucleotide probes having DNA sequences selected from a group containing SEQ ID NOs. 4–15.

18. A method as claimed in claim 1 wherein said second test array of oligonucleotide probes having DNA sequences selected from a group containing SEQ ID NOs. 16–46.

19. A method as claimed in claim 1 wherein said fluorescent hybridization signal is detectable by a scanning device.

* * * * *

UNITED STATES PATENT AND TRADEMARK OFFICE
CERTIFICATE OF CORRECTION

PATENT NO.    : 6,902,894 B2
DATED         : June 7, 2005
INVENTOR(S)   : Yang et al.

It is certified that error appears in the above-identified patent and that said Letters Patent is hereby corrected as shown below:

<u>Columns 11 and 12,</u>
Table 1, line 20, "W10" should be -- W9 --.

<u>Column 30,</u>
Line 31, "950°" should be -- 95° --.

Signed and Sealed this

Sixth Day of September, 2005

JON W. DUDAS
*Director of the United States Patent and Trademark Office*

SEQUENCE LISTING

<160> NUMBER OF SEQ ID NOS: 53

<210> SEQ ID NO 1
<211> LENGTH: 16
<212> TYPE: DNA
<213> ORGANISM: Artificial Sequence
<220> FEATURE:
<223> OTHER INFORMATION: PCR primer

<400> SEQUENCE: 1
acctccagcc cggcac                                                             16

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
cgccgcgatc aaggagtt                                                           18

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
agccgatcag accgatgttg                                                         20

<210> SEQ ID NO 4
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 4
aggagttctt cggca                                                              15

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 5
agccagctga gccaa                                                              15

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 6
cagctgagcc aattc                                                              15

<210> SEQ ID NO 7
<211> LENGTH: 15

```
<212> TYPE: DNA
<213> ORGANISM: Artificial Sequence
<220> FEATURE:
<223> OTHER INFORMATION: Oligonucleotide probe

<400> SEQUENCE: 7
gctgagccaa ttcat                                                    15

<210> SEQ ID NO 8
<211> LENGTH: 16
<212> TYPE: DNA
<213> ORGANISM: Artificial Sequence
<220> FEATURE:
<223> OTHER INFORMATION: Oligonucleotide probe

<400> SEQUENCE: 8
gccaattcat ggacca                                                   16

<210> SEQ ID NO 9
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 9
ttcatggacc agaac                                                    15

<210> SEQ ID NO 10
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 10
cccgctgtcg gggtt                                                    15

<210> SEQ ID NO 11
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 11
gggttgaccc acaag                                                    15

<210> SEQ ID NO 12
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 12
ttgacccaca agcgc                                                    15

<210> SEQ ID NO 13
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 13
```

-continued aagcgccgac tgtcg                                                15

<210> SEQ ID NO 14
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 14
cgactgtcgg cgctg                                                15

<210> SEQ ID NO 15
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 15
tcggcgctgg ggccc                                                15

<210> SEQ ID NO 16
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 16
agccagccga gccaa                                                15

<210> SEQ ID NO 17
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 17
agccagcgga gccaa                                                15

<210> SEQ ID NO 18
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 18
cagctgaccc aattc                                                15

<210> SEQ ID NO 19
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 19
gctgagcgaa ttcat                                                15

<210> SEQ ID NO 20
<211> LENGTH: 15
<212> TYPE: DNA
<213> ORGANISM: Artificial Sequence

```
<220> FEATURE:
<223> OTHER INFORMATION: Oligonucleotide probe

<400> SEQUENCE: 20
ctgagcccat tcatg                                                          15

<210> SEQ ID NO 21
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 21
ctgagcctat tcatg                                                          15

<210> SEQ ID NO 22
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 22
agccaattct tcatg                                                          15

<210> SEQ ID NO 23
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 23
gccaattcat gttca                                                          15

<210> SEQ ID NO 24
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 24
ctgagcctgg accag                                                          15

<210> SEQ ID NO 25
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 25
ctgagccacc agaac                                                          15

<210> SEQ ID NO 26
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 26
attcatgaac aaccc                                                          15
```

<210> SEQ ID NO 27
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 27
ggaccagaac ccgct                                                    15

<210> SEQ ID NO 28
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 28
ccaattcgtg gacca                                                    15

<210> SEQ ID NO 29
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 29
attcatgtac cagaa                                                    15

<210> SEQ ID NO 30
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 30
ttcatggtcc agaac                                                    15

<210> SEQ ID NO 31
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 31
ttcatggccc agaac                                                    15

<210> SEQ ID NO 32
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 32
attcatgaac cagaa                                                    15

<210> SEQ ID NO 33
<211> LENGTH: 15
<212> TYPE: DNA
<213> ORGANISM: Artificial Sequence
<220> FEATURE:
<223> OTHER INFORMATION: Oligonucleotide probe

```
<400> SEQUENCE: 33
cccgctgcag gggtt                                                        15

<210> SEQ ID NO 34
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 34
gttgaccacc aagcg                                                        15

<210> SEQ ID NO 35
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 35
ttgaccccca agcgc                                                        15

<210> SEQ ID NO 36
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 36
ttgacccgca agcgc                                                        15

<210> SEQ ID NO 37
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 37
ttgaccctca agcgc                                                        15

<210> SEQ ID NO 38
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 38
ttgacctgca agcgc                                                        15

<210> SEQ ID NO 39
<211> LENGTH: 14
<212> TYPE: DNA
<213> ORGANISM: Artificial Sequence
<220> FEATURE:
<223> OTHER INFORMATION: Oligonucleotide probe

<400> SEQUENCE: 39
ttgacctaca agcg                                                         14

<210> SEQ ID NO 40
```

```
<211> LENGTH: 14
<212> TYPE: DNA
<213> ORGANISM: Artificial Sequence
<220> FEATURE:
<223> OTHER INFORMATION: Oligonucleotide probe

<400> SEQUENCE: 40
gttgacctac aagc                                                        14

<210> SEQ ID NO 41
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 41
gttgacttac aagcg                                                       15

<210> SEQ ID NO 42
<211> LENGTH: 14
<212> TYPE: DNA
<213> ORGANISM: Artificial Sequence
<220> FEATURE:
<223> OTHER INFORMATION: Oligonucleotide probe

<400> SEQUENCE: 42
ttgaccgaca agcg                                                        14

<210> SEQ ID NO 43
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 43
aagcgccaac tgtcg                                                       15

<210> SEQ ID NO 44
<211> LENGTH: 13
<212> TYPE: DNA
<213> ORGANISM: Artificial Sequence
<220> FEATURE:
<223> OTHER INFORMATION: Oligonucleotide probe

<400> SEQUENCE: 44
gactgttggc gct                                                         13

<210> SEQ ID NO 45
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 45
cgactgtgtg cgctg                                                       15

<210> SEQ ID NO 46
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 46
```

```
tcggcgccgg ggccc                                            15
```

<210> SEQ ID NO 47
<211> LENGTH: 15
<212> TYPE: DNA
<213> ORGANISM: Artificial Sequence
<220> FEATURE:
<223> OTHER INFORMATION: Oligonucleotide probe

<400> SEQUENCE: 47

```
gtctgtcacg tgagc                                            15
```

<210> SEQ ID NO 48
<211> LENGTH: 16
<212> TYPE: DNA
<213> ORGANISM: Artificial Sequence
<220> FEATURE:
<223> OTHER INFORMATION: PCR primer

<400> SEQUENCE: 48

```
gctgtcgggg ttgacc                                           16
```

<210> SEQ ID NO 49
<211> LENGTH: 31
<212> TYPE: DNA
<213> ORGANISM: Artificial Sequence
<220> FEATURE:
<223> OTHER INFORMATION: PCR primer

<400> SEQUENCE: 49

```
tttttttttt tttttggtca accccgacag c                          31
```

<210> SEQ ID NO 50
<211> LENGTH: 12
<212> TYPE: DNA
<213> ORGANISM: Artificial Sequence
<220> FEATURE:
<223> OTHER INFORMATION: PCR primer

<400> SEQUENCE: 50

```
ggccccagcg cc                                               12
```

<210> SEQ ID NO 51
<211> LENGTH: 27
<212> TYPE: DNA
<213> ORGANISM: Artificial Sequence
<220> FEATURE:
<223> OTHER INFORMATION: PCR primer

<400> SEQUENCE: 51

```
tttttttttt tttttggcgc tggggcc                               27
```

<210> SEQ ID NO 52
<211> LENGTH: 17
<212> TYPE: DNA
<213> ORGANISM: Artificial Sequence
<220> FEATURE:
<223> OTHER INFORMATION: PCR primer

<400> SEQUENCE: 52

```
gctgagccaa ttcatgg                                          17
```

<210> SEQ ID NO 53
<211> LENGTH: 32
<212> TYPE: DNA

-continued

```
<213> ORGANISM: Artificial Sequence
<220> FEATURE:
<223> OTHER INFORMATION: PCR primer

<400> SEQUENCE: 53
tttttttttt tttttccatg aattggctca gc                                    32
```